(12) United States Patent
Pfeffer et al.

(10) Patent No.: US 10,172,537 B2
(45) Date of Patent: *Jan. 8, 2019

(54) ROD-SHAPED BODY

(71) Applicant: MARVIS MEDICAL GMBH, Frechen (DE)

(72) Inventors: Joachim-Georg Pfeffer, Aachen (DE); Rolf W. Günther, Aachen (DE); Thomas Schmitz Rode, Aachen (DE)

(73) Assignee: MARVIS INTERVENTIONAL GMBH, Frechen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/710,734

(22) Filed: May 13, 2015

(65) Prior Publication Data

US 2015/0245783 A1 Sep. 3, 2015

Related U.S. Application Data

(63) Continuation-in-part of application No. 11/993,658, filed as application No. PCT/DE2006/001094 on Jun. 26, 2006, now Pat. No. 9,038,639.

(30) Foreign Application Priority Data

Jun. 28, 2005 (DE) .................. 10 2005 030 472

(51) Int. Cl.
*A61B 5/055* (2006.01)
*A61L 29/12* (2006.01)
(Continued)

(52) U.S. Cl.
CPC ............ *A61B 5/055* (2013.01); *A61L 29/126* (2013.01); *A61L 29/18* (2013.01); *A61L 31/026* (2013.01);
(Continued)

(58) Field of Classification Search
CPC ............ A61M 25/005; A61M 25/0108; A61M 2025/1079; A61B 19/54; A61B 8/12; A61B 6/12

See application file for complete search history.

(56) References Cited

U.S. PATENT DOCUMENTS 4,257,421 A 3/1981 Beal
4,657,024 A * 4/1987 Coneys ............. A61M 25/0108
138/118

(Continued)

FOREIGN PATENT DOCUMENTS

DE 20019484 11/2000
DE 10107750 11/2003
(Continued)

OTHER PUBLICATIONS

Konings, M.K. et al. (2001) Catheters and guidewires in interventional MRI: problems and solutions. Medical Mundi, 45:1.

*Primary Examiner* — Christine H Matthews
(74) *Attorney, Agent, or Firm* — Tristan A. Fuierer; Marianne Fuierer; Olive Law Group, PLLC

(57) ABSTRACT

The invention relates to a rod-shaped body comprised of one or more filaments and of a non-ferromagnetic matrix material. The matrix material surrounds the filament(s) and/or adheres them to one another. The rod-shaped body is also comprised of a dopant consisting of particles that generate magnetic resonance tomographic artifacts that is introduced into the matrix material. Rod-shaped bodies of this type can be used to construct guide wires, catheters and other instruments to be used in minimally invasive surgical interventions.

37 Claims, 5 Drawing Sheets

(51) Int. Cl.
  *A61L 29/18* (2006.01)
  *A61L 31/12* (2006.01)
  *A61L 31/18* (2006.01)
  *A61L 31/02* (2006.01)
  *A61L 31/04* (2006.01)
  *A61M 25/09* (2006.01)

(52) U.S. Cl.
  CPC .......... *A61L 31/048* (2013.01); *A61L 31/125* (2013.01); *A61L 31/18* (2013.01); *A61M 25/09* (2013.01); *A61M 2025/09133* (2013.01)

(56) References Cited

U.S. PATENT DOCUMENTS

| | | | |
|---|---|---|---|
| 5,154,179 | A | 10/1992 | Ratner |
| 5,251,640 | A | 10/1993 | Osborne |
| 5,705,014 | A | 1/1998 | Scheneck et al. |
| 5,897,696 | A * | 4/1999 | Giordano ................ A61L 31/08 106/181.1 |
| 6,574,497 | B1 | 6/2003 | Pacetti |
| 2003/0055449 | A1 | 3/2003 | Lee et al. |
| 2004/0185179 | A1 | 9/2004 | Conners, III et al. |

FOREIGN PATENT DOCUMENTS

| | | |
|---|---|---|
| EP | 0894503 | 6/1998 |
| EP | 1206945 | 5/2002 |
| EP | 1388346 | 2/2004 |
| WO | WO 02/058779 | 8/2002 |
| WO | WO 03/000307 | 1/2003 |

\* cited by examiner

ROD-SHAPED BODY

CROSS REFERENCE TO RELATED APPLICATIONS

The present application is a Continuation-in-Part application of copending U.S. patent application Ser. No. 11/993,658, now U.S. Pat. No. 9,038,639 which in turn claims priority to PCT Application No. PCT/DE2006/001094 filed on Jun. 26, 2006, which in turn claims priority to German Patent Application No. DE 10 2005 030 472.9 filed on Jun. 28, 2005, the contents of all applications are hereby incorporated by reference herein.

BACKGROUND OF THE INVENTION

Technical Field

The invention relates to the field of devices, in particular guidewires and catheters, needed for minimally invasive interventions.

Related Art

Minimally invasive interventions in the human body require guidewires and catheters. These are available in a multitude of forms, sizes, configurations and mechanical characteristics for procedures guided by X-ray imaging.

These catheters and guidewires are not applicable to magnetic resonance tomography (MRT)—guided procedures as they usually contain metals. This leads to artifacts which makes evaluation of the images difficult or even impossible. Furthermore, this conceals the risk of inductive heating in the magnetic field leading to a potential risk to the patient.

Three essential requirements have to be fulfilled by devices to make them suitable for use in MRT:
 1. They must not contain any long metal parts, e.g. metal fabric for catheter reinforcement or wire cores for guidewires.
 2. They need to be visible over optimally their full length in the MRT image so that the position of the device is clear in relation to the organ(s).
 3. As the local resolution in real-time MRT currently does not allow a direct imaging of catheters and guidewires, clearly visible effects have to be generated along the length of the device.

Such effects on the one hand should be strong enough to render the device well visible in the MRT image but on the other hand weak enough not to make important structures in the vicinity unidentifiable.

The strong magnetic field of a magnetic resonance tomography makes the absence of any ferromagnetism a precondition for the use of devices within this equipment. This excludes e.g. many standard catheters which can be attracted and misguided by the strong magnetic field. Materials solely composed of polymers fulfill the prerequisite of absence of ferromagnetism.

The minimal size of devices used for intervention such as guidewires or catheters causes a special problem for application in magnetic resonance tomography and especially for rapid imaging. The faster imaging is done in MRT the lower is the local resolution. In order to make visible such a small item as a catheter which shows up as a dark object due to the relative lack of hydrogen protons, appropriate high-resolution and thus slow imaging is necessary. Furthermore, it is very difficult to make visible such a small item in the usually prepared layer thickness of around 10 mm so that on the one hand it is positioned within the recorded layer and on the other hand it does not become invisible due to partial volume effects.

A solution to this problem resides in markers which lead to a local extinction of the signals in the MRT image and therefore allow easier identification and visualization of the device. For this purpose generally materials which possess a susceptibility (magnetizability) different from water are suitable. The markers have to be applied locally in order to avoid dependence of the marker on the orientation of a device in the main magnetic field. Rare earths which are used as MRT contrast agents have been used for this purpose in higher concentrations. They have been applied or introduced, both locally as markers as well as for catheter fillings to obtain better visibility of devices in the MRT.

A major disadvantage of these substances used so far as local markers resides in their rather high mass required to achieve a sufficient marking effect in the MRT. This is reflected e.g. in the fact that much more complicated techniques for conducting current along a wire within the device, or which mount micro-inductors on the catheter, have been developed although resultant safety issues such as heating from the radio frequency field have not yet been resolved at all. These heating effects occur when electric conductors such as metals are exposed to the radio frequency field over a longer distance in the MR tomograph. If resonance occurs, a summation of the irradiated radio energy over a standing wave results, with the possible consequence of a substantial heating of the conductor.

Known single-stranded homogenous non-metal materials exhibit major disadvantages of their material characteristics in comparison to common metal cores regarding stability, flexibility and elasticity, e.g., materials with high stability mostly possess low flexibility and/or elasticity. Consequently it has not been possible to date to replace the common metal core by an MRT compatible and visible material.

SUMMARY OF THE INVENTION

It is an object of the present invention to provide MRT-compatible devices, especially a catheter and a guidewire, which do not contain longer coherent metallic parts and thus do not suffer from the risk of inductive heating. On the other hand the device shall be visible in appropriate MRT sequences over its complete length along and across the main magnetization without having body structures in the vicinity of the device made unrecognizable as a result of artefacts. A further object of this invention is that of providing MRT-compatible devices which do not suffer from any limitations in material characteristics and handling properties as compared to currently known devices.

As a solution to this problem a rod-shaped body ("rod") is suggested which is composed of one or more non-metallic filaments and a non-ferromagnetic matrix material wherein the matrix material encloses and/or agglutinates the filament(s), and wherein a doping by particles producing artefacts in magnetic resonance tomography is included into the matrix material. The combination of the matrix material with the non-metallic filament(s) results in an unexpectedly simple manner in metal-like stiffness, flexibility and elasticity characteristics.

The filaments forming the rod-shaped body can be produced easily and cost-efficiently, with adequate stability and the ability to transmit compressive and tensile force and torques. By doping of the matrix material which is either necessary for enclosure of a single filament or agglutination of several filaments, a simple and efficient method has been developed to visualize the rod-shaped body in the MRT and at the same time to allow handling according to current standards.

The actual devices such as catheters, guidewires, etc. are constructed from these basic elements as described below. Advantageous developments of the invention are the subject of the dependent claims.

It is especially advantageous if the filaments are made of plastic and/or glass fibre. Such filaments can be easily and cost-efficiently produced with great length and a wide variety of cross-sections and diameters. Especially glass fibre has minimal elongation, making possible very direct transmission of force and momentum.

The matrix material may advantageously be made of epoxy resin. Epoxy resins are available with a wide range of properties and machines for their processing are well-developed.

The rods can be continuously doped along their longitudinal axis with particles generating artefacts in magnetic resonance tomography. This makes the rod well visible in the MRT over its entire length.

For some applications, however, it may be preferred to dope the rod in a discontinuous manner, particularly in sections along its longitudinal axis, with particles generating artefacts in magnetic resonance tomography. This especially applies to the tips of the rods which need to be exceptionally visible in some cases.

Within the rods the filaments can be arranged in parallel. This supports especially simple processing.

The filaments also can be arranged braided with each other, woven, cross-linked, twisted or coiled in especially preferred embodiments in order to realize certain favoured characteristics, especially mechanical properties.

It is advantageous if the mass of a single particle is in the range of micrograms to nanograms and, due to the minimal amount in relation to the matrix material, does not substantially influence the outer shape, stability and the torquing characteristics of the rod.

Typically preferred sizes of the rods are in the diameter range of between 0.005 and 5 mm, preferably between 0.1 and 1 mm.

A cylindrical composite body ("cylinder"), particularly a guidewire, is constructed from the described rods in such a manner that at least one rod is enclosed by a non-ferromagnetic matrix material or several rods are enclosed and/or agglutinated by a non-ferromagnetic matrix material.

In this way cylinders of widely varying geometries and mechanical as well as MRTrelated characteristics can be easily and cost-efficiently constructed with one and the same element (the rod) and the matrix material.

The cylinder may e.g. most simply be built from rods of the same diameter or—in another embodiment—from rods of different diameters. The latter embodiment in particular may have two rods of smaller diameter arranged around a first rod. The individual rods can—similar to the filaments as before—be arranged braided with each other, woven, cross-linked, twisted or coiled.

In a particularly preferred embodiment the cylinders contain rods with different magnetic resonance tomographic properties. For instance the same cylinder (e.g. as a guidewire) can be visualized equally well in different MRT sequences (e.g. for specific visualization of fatty tissue, muscle tissue, etc.).

It is advantageous to cover the outer surface of the cylinder with a hydrophilic coating thus making it biocompatible.

It is however also possible to construct other devices from the described rods, particularly a tube-shaped composite body ("catheter"). This is composed of at least one rod which is enclosed by a non-ferromagnetic matrix material and/or several rods bonded together and/or enclosed.

In an embodiment of the catheter this is comprised of several rods which are embedded in a radial distribution in the periphery of its wall. Especially for achieving symmetrical properties these can be embedded in a regular radial distribution.

For the same reason the rods forming the catheter can possess the same diameter. In special cases however rods of different diameter can also be used.

Similarly to the cylinders and guidewires, in the case of the catheter rods can be arranged braided with each other, woven, cross-linked, twisted or coiled in the catheter and can possess different magnetic resonance tomographic properties. The outer surface of the catheter can be hydrophilically coated.

Besides the above described devices other devices can be constructed from rod-shaped bodies and the matrix material in similar manner, e.g. Dormia baskets.

Preferred embodiments of the invention are described below with the aid of the enclosed schematic drawings.

DETAILED DESCRIPTION OF THE INVENTION

Figure 1:
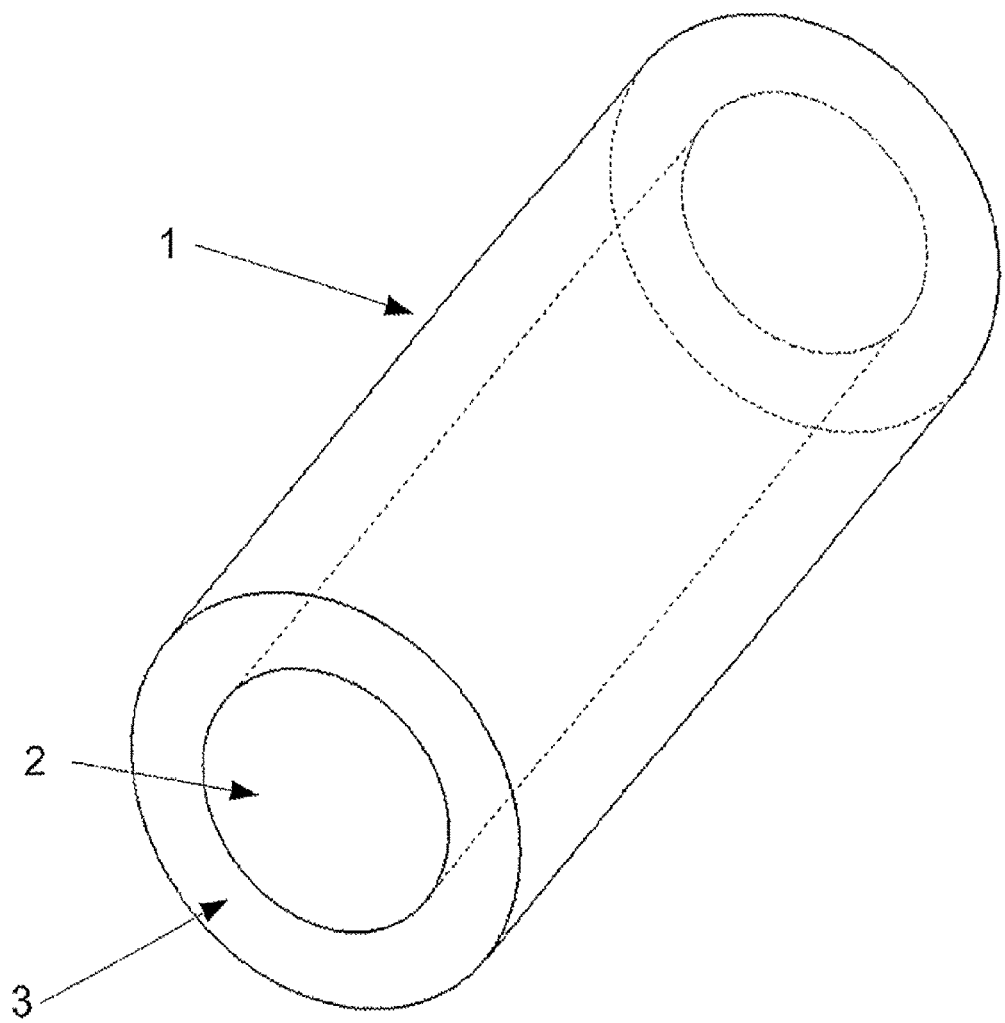
FIG. 1 shows a doped rod of the present invention.

The rod 1 and section of a rod respectively shown in FIG. 1 consist of an elongated glass fibre filament 2 which is embedded in epoxy resin 3 as the matrix material. The rod 1 can be produced using common techniques, particularly by extrusion so as to be virtually endless. After extrusion it may be cut to the length required for further processing.

Particles producing magnetic resonance tomographic artefacts, e.g. nanoparticles,—not shown—are included in the epoxy resin. These are homogenously distributed in the matrix material so that a rod 1 homogenously doped along its longitudinal axis results.

Figure 4:
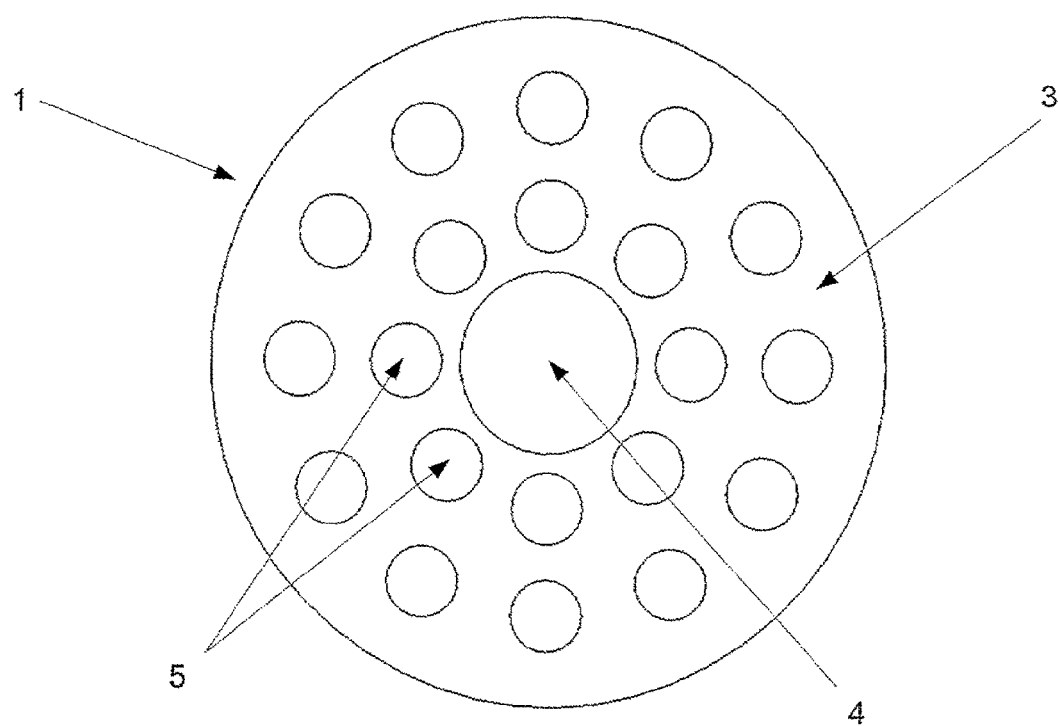
FIG. 4 shows a cross-section through a doped rod.

As shown in FIG. 4 instead of one filament also several filaments 4, 5 can be arranged in a rod-shaped body 1. In the example shown this is a rather thick filament 4 and arranged around this are rather thin filaments 5. All filaments 4, 5 are agglutinated with and encompassed by the epoxy resin 3.

Figure 2:
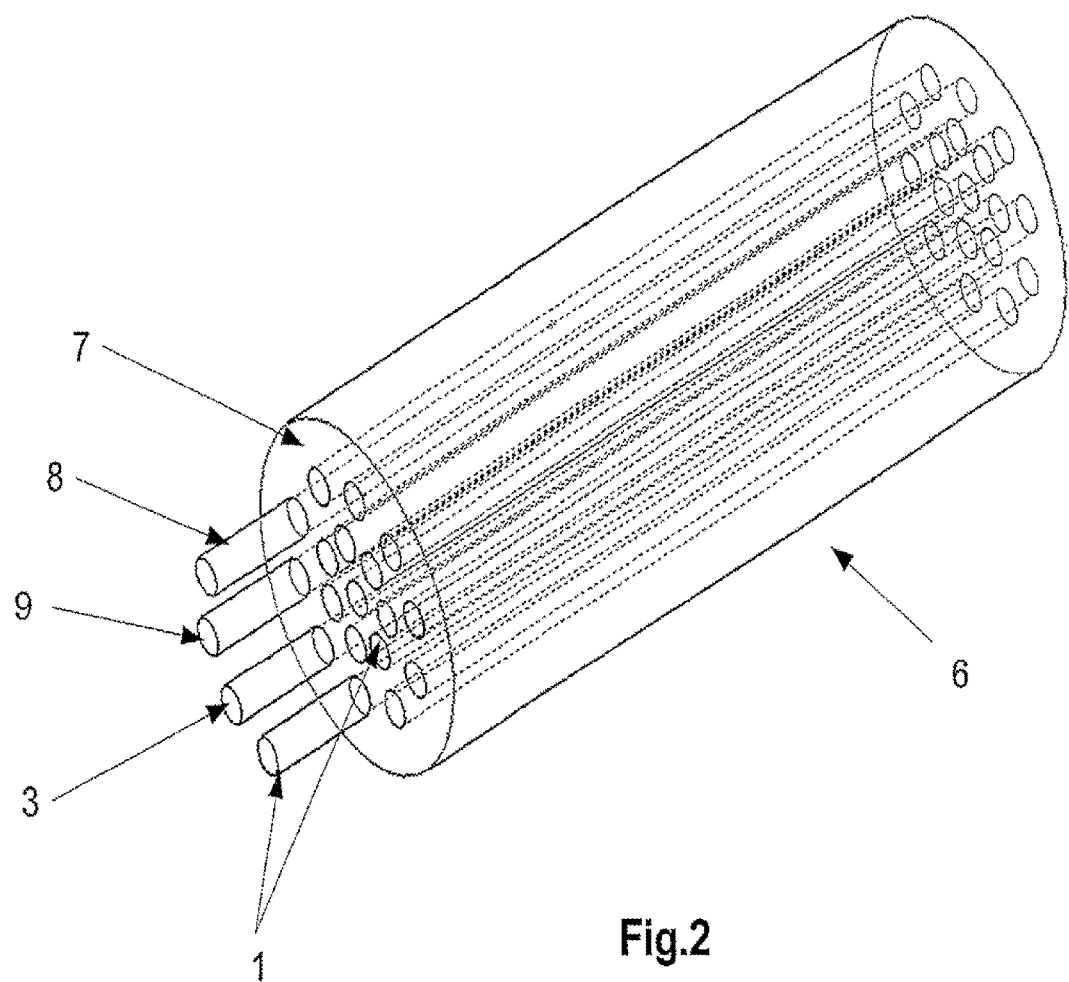
FIG. 2 shows a cylindrical composite body (guidewire).

In FIG. 2, a cylindrical composite body 6 and a section of this are shown. The lengthwise extension can be significantly longer, amounting to e.g. several meters with a diameter of e.g. 0.1 mm.

The cylindrical composite body 6 is constructed from several rods 1 which are agglutinated and enclosed by a matrix material 7, e.g. an epoxy resin. This matrix material 7 is, in contrast to the matrix material 4, not doped with particles producing magnetic resonance tomographic artefacts. The visibility of the cylindrical composite body 6 in the MRT relies solely on the visibility of the embedded rods 1. In the depicted embodiment, rods 1, 8, 9 with different dopings are included so that, depending on the sequence, different rods 1, 8, 9 become visible in the MRT.

Figure 3:
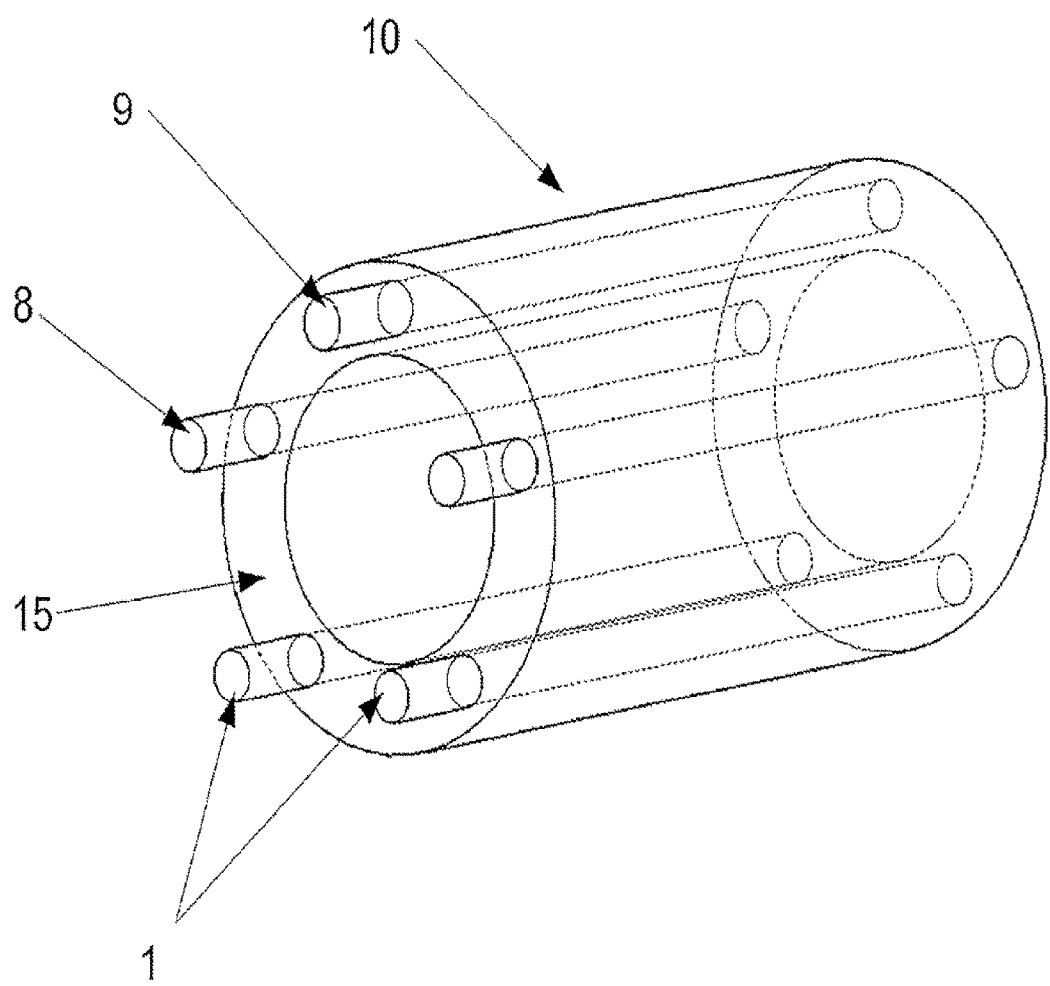
FIG. 3 shows a tube-shaped composite body (catheter).

In the same way, as shown in FIG. 3, a tube-shaped composite body 10 can also be constructed (once again only a section is shown here).

The tube-shaped composite body 10 is similarly constructed from a shell material 15 and several rods 1, 8, 9 with different doping. All rods are evenly distributed around the periphery of the tube-shaped composite body 10.

The cylindrical composite body 6 as well as the tube-shaped composite body 10 can be covered with a hydrophilic coating, which is not shown.

Figure 5:
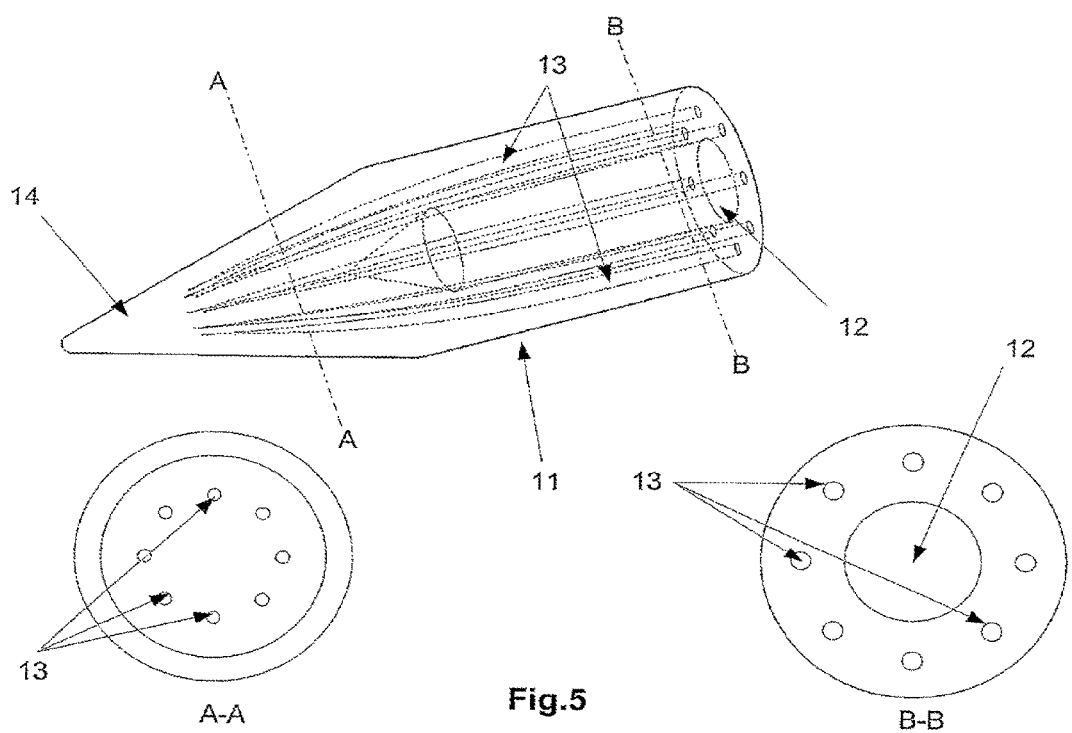
FIG. 5 shows the tip of a guidewire.

The ends of the cylindrical and tube-shaped composite bodies 6, 10 can be treated in an appropriate manner, e.g. rounded, polished or capped. As shown in FIG. 5, particularly the inner rod 12, in a guidewire 11 with an inner rod 12 and radially distributed outer rods 13, can be shorter than the outer rods 13. These are brought together and form a tip 14 (arrangement of the rods 12 and 13 as displayed in the cross-sections A-A and B-B respectively).

That which is claimed is:

1. A rod-shaped body for manufacturing a medical instrument comprising:
   one or more non-metallic filaments; and
   a non-ferromagnetic matrix material consisting essentially of epoxy resin and a multiplicity of doping particles, wherein the non-ferromagnetic matrix material encloses and/or agglutinates the one or more non-metallic filaments, wherein the multiplicity of doping particles are distributed in the non-ferromagnetic matrix material, and wherein the doping particles generate magnetic resonance tomography artefacts.

2. The rod-shaped body according to claim 1, wherein the medical instrument is a catheter or a guidewire.

3. The rod-shaped body according to claim 1, wherein the one or more non-metallic filaments consist of plastic and/or glass fibre.

4. The rod-shaped body according to claim 1 wherein the doping particles are included continuously along the longitudinal axis of the rod-shaped body.

5. The rod-shaped body according to claim 1, wherein the doping particles are included discontinuously along the longitudinal axis of the rod shaped body.

6. The rod-shaped body according to claim 1, wherein the one or more non-metallic filaments are arranged in parallel.

7. The rod-shaped body according to claim 1, wherein the one or more non-metallic filaments are braided with each other, woven, cross-linked, twisted or coiled.

8. The rod-shaped body according to claim 1, wherein a single particle of the multiplicity of doping particles has a mass in the range of micrograms to nanograms and, due to a minimal amount in relation to the non-ferromagnetic matrix material, does not substantially influence outer shape, stability or torquing characteristics of the rod-shaped body.

9. The rod-shaped body according to claim 1, having a diameter in the range of between 0.005 mm and 5 mm or between 0.1 and 1 mm.

10. The rod-shaped body according to claim 1, wherein the doping particles do not substantially influence outer shape, stability or torquing characteristics.

11. The rod-shaped body according to claim 1, wherein the rod-shaped body has a substantially smooth surface.

12. A guidewire consisting of:
    at least one rod-shaped body consisting essentially of:
        one or more non-metallic filaments;
        a non-ferromagnetic matrix material, wherein the non-ferromagnetic matrix material encloses and/or agglutinates the one or more non-metallic filaments; and
        a multiplicity of doping particles distributed in the non-ferromagnetic matrix material, wherein the doping particles generate magnetic resonance tomography artefacts; and
    a non-ferromagnetic shell material, wherein the shell material encloses and/or agglutinates the at least one rod-shaped body.

13. The guidewire according to claim 12 consisting of several rod-shaped bodies having the same diameter or different diameters.

14. The guidewire according to claim 12 consisting of several rod-shaped bodies where a first rod-shaped body of the at least one rod-shaped body is surrounded with at least one secondary rod-shaped body of the at least one rod-shaped body having a smaller diameter.

15. The guidewire according to claim 14, wherein the at least one secondary rod-shaped body is braided, woven, cross-linked, twisted or coiled around the first rod-shaped body.

16. The guidewire according to claim 12, consisting of several different rod-shaped bodies wherein the different rod-shaped bodies possess different magnetic resonance tomography properties.

17. The guidewire according to claim 12 having an outer surface and wherein the outer surface is covered with a hydrophilic coating.

18. The guidewire according to claim 12, wherein the non-ferromagnetic matrix material comprises epoxy resin.

19. A catheter consisting of:
    at least one rod-shaped body, consisting essentially of:
        one or more non-metallic filaments;
        a non-ferromagnetic matrix material, wherein the non-ferromagnetic matrix material encloses and/or agglutinates the one or more non-metallic filaments; and
        a multiplicity of doping particles distributed in the non-ferromagnetic matrix material, wherein the doping particles generate magnetic resonance tomography artefacts; and
    a non-ferromagnetic shell material, wherein the shell material encloses and/or agglutinates the at least one rod-shaped body.

20. The catheter according to claim 19, consisting of several rod-shaped bodies that are peripherally embedded in a radial distribution in the catheter.

21. The catheter according to claim 20, wherein the rod-shaped bodies are embedded in a regular radial distribution.

22. The catheter according to claim 19, consisting of several rod-shaped bodies wherein the rod-shaped bodies have the same or different diameters.

23. The catheter according to claim 19, consisting of several rod-shaped bodies wherein the rod-shaped bodies are braided with each other, woven, cross-linked, twisted or coiled.

24. The catheter according to claim 19, consisting of several different rod-shaped bodies wherein the different rod-shaped bodies possess different magnetic resonance tomography properties.

25. The catheter according to claim 19, having an outer surface wherein the outer surface is covered with a hydrophilic coating.

26. A cylindrical composite body comprising a multiplicity of rod-shaped bodies used for manufacturing a magnetic resonance tomography (MRT)-compatible medical instrument, wherein at least one of the rod-shaped bodies is comprised of:
    one or more non-metallic filaments;

a non-ferromagnetic matrix material, wherein the non-ferromagnetic matrix material encloses and/or agglutinates the one or more non-metallic filaments; and doping particles distributed in the non-ferromagnetic matrix material, wherein the doping particles generate magnetic resonance tomography (MRT) artefacts thereby forming a doped matrix material wherein each of the doping particles has a mass in the range of micrograms to nanograms, wherein the multiplicity of rod-shaped bodies have the same diameters, different diameters, or a first rod-shaped body of the multiplicity of rod-shaped bodies is surrounded by several secondary rod-shaped bodies of smaller diameters, and wherein the multiplicity of rod-shaped bodies is surrounded by a non-doped shell material.

27. The cylindrical composite body according to claim 26 wherein the medical instrument is a catheter or a guidewire.

28. The cylindrical composite body according to claim 26 wherein the one or more non-metallic filaments consists of plastic and/or glass fibre.

29. The cylindrical composite body according to claim 26 wherein the non-ferromagnetic matrix material consists of epoxy resin.

30. The cylindrical composite body according to claim 26 wherein at least one of the rod-shaped bodies is continuously doped along its longitudinal axis with said doping particles.

31. The cylindrical composite body according to claim 26 wherein at least one of the rod-shaped bodies is discontinuously doped along its longitudinal axis, in sections, with said doping particles.

32. The cylindrical composite body according to claim 26 wherein the one or more non-metallic filaments are arranged in parallel.

33. The cylindrical composite body according to claim 26, consisting of several non-metallic filaments, wherein the non-metallic filaments are braided with each other, woven, cross-linked, twisted or coiled.

34. The cylindrical composite body according to claim 26 wherein the doping particles do not substantially influence outer shape, stability or torquing characteristics of the multiplicity of rod-shaped bodies.

35. The cylindrical composite body according to claim 26 wherein a diameter of the rod shaped-bodies is in the range of between 0.005 mm and 5 mm or in in the range of between 0.1 and 1 mm.

36. A cylindrical composite body comprising a multiplicity of rod-shaped bodies, wherein at least one of the rod-shaped bodies is comprised of one or more non-metallic filaments, a non-ferromagnetic matrix material, wherein the non-ferromagnetic matrix material encloses and/or agglutinates the one or more non-metallic filaments; and doping particles included in the non-ferromagnetic matrix material, wherein the doping particles generate magnetic resonance tomography (MRT) artefacts thereby forming the doped matrix material, wherein each of the doping particles has a mass in the range of micrograms to nanograms, wherein the multiplicity of rod-shaped bodies have the same diameters or different diameters or a first rod-shaped body of the multiplicity of rod-shaped bodies is surrounded by several secondary rod-shaped bodies of smaller diameters, and wherein the multiplicity of rod-shaped bodies is surrounded by a non-doped shell material.

37. A guidewire consisting of:

at least one rod-shaped body comprising:

one or more non-metallic filaments;

a non-ferromagnetic matrix material, wherein the non-ferromagnetic matrix material encloses and/or agglutinates the one or more non-metallic filaments; and a multiplicity of doping particles distributed in the non-ferromagnetic matrix material, wherein the doping particles generate magnetic resonance tomography artefacts; and a non-ferromagnetic shell material, wherein the shell material encloses and/or agglutinates the at least one rod-shaped body, wherein a first rod-shaped body of the at least one rod-shaped body is surrounded with at least one secondary rod-shaped body of the at least one rod-shaped body having a smaller diameter.

\* \* \* \* \*